United States Patent [19]
Bittman et al.

[11] Patent Number: 6,058,649
[45] Date of Patent: May 9, 2000

[54] SEED COATING FOR ENHANCING THE LEVEL OF SELENIUM IN CROPS

[75] Inventors: Shabtai Bittman, Abbotsford; Wayne T. Buckley, Brandon; Kevin Zaychuk; E. A. P. Brown, both of Edmonton, all of Canada

[73] Assignees: Her Majesty the Queen in right of Canada, as represented by the Minister of Agriculture; Agra-Food Canada, both of British Columbia, Canada

[21] Appl. No.: 08/862,511

[22] Filed: May 23, 1997

Related U.S. Application Data

[63] Continuation-in-part of application No. 08/555,758, Sep. 11, 1995.

[30] Foreign Application Priority Data

Oct. 24, 1995 [CA] Canada ................................. 2161294

[51] Int. Cl.⁷ .................................................... A01C 1/06
[52] U.S. Cl. ............................................. 47/57.6; 435/410
[58] Field of Search ................................ 47/57.6; 435/410

[56] References Cited

U.S. PATENT DOCUMENTS

| | | |
|---|---|---|
| 3,698,133 | 10/1972 | Schreiber . |
| 3,808,740 | 5/1974 | Porter et al. . |
| 3,905,152 | 9/1975 | Loperfido . |
| 3,911,183 | 10/1975 | Hinkes . |
| 3,950,891 | 4/1976 | Hinkes . |
| 4,149,869 | 4/1979 | Lloyd . |
| 4,251,952 | 2/1981 | Porter et al. . |
| 4,299,613 | 11/1981 | Cardarelli . |
| 4,367,609 | 1/1983 | Lloyd . |
| 4,388,303 | 6/1983 | Allan . |
| 4,447,984 | 5/1984 | Sampson et al. . |
| 4,493,162 | 1/1985 | Langan et al. . |
| 4,656,038 | 4/1987 | Baugh . |
| 4,735,015 | 4/1988 | Schmolka . |
| 4,735,017 | 4/1988 | Gago et al. . |
| 4,847,087 | 7/1989 | Young . |
| 4,879,839 | 11/1989 | Gago et al. . |
| 4,880,628 | 11/1989 | Allen et al. . |
| 5,006,149 | 4/1991 | Kiss et al. . |
| 5,017,374 | 5/1991 | Humphrey . |
| 5,026,417 | 6/1991 | Kucey . |
| 5,041,290 | 8/1991 | Gindrat . |
| 5,044,116 | 9/1991 | Gago et al. . |
| 5,106,648 | 4/1992 | Williams . |
| 5,113,619 | 5/1992 | Leps et al. . |
| 5,119,589 | 6/1992 | Rowse . |
| 5,169,647 | 12/1992 | Young . |
| 5,300,127 | 4/1994 | Williams . |

FOREIGN PATENT DOCUMENTS

| | | |
|---|---|---|
| 542745 | 6/1957 | Canada . |
| 1229497 | 11/1987 | Canada . |
| 1329491 | 2/1989 | Canada . |
| 2007277 | 1/1990 | Canada . |
| 2042661 | 11/1991 | Canada . |

OTHER PUBLICATIONS

"The effects of sodium selenate applications on growth and selenium concentration in wheat", *New Zealand Journal of Crop and Horticultural Science*, (1989), vol. 17, 229–237.

Gunnar Gissel–Nielson et al., Selenium in Soils and Plants and Its Importance in Livestock and Human Nutrition; Advances in Agronomy, vol. 37 (1984).

J.H. Watkinson, Prevention of Selenium Deficiency in Grazing Animals by Annual Topdressing of Pasture With Sodium Selenate; New Zealand Veterinary Journal, vol. 31, pp. 78–85.

Toivo Ylaranta, Effect of Applied Selenite and Selenate on the Content of Barley (Hordeum Vul Vulgare); Annales Agiculturae Fenniae, vol. 22, pp. 164–174 (1983).

Gupta, U.C., et al., Effect of Treating Forage Seed with Selenium on the Selenium Concentration of Alfalf and Westerwolds Ryegrass; Can. J. Soil Sci. vol. 63, pp. 641–643, Aug. (1993).

*Primary Examiner*—Leon B. Lankford, Jr.
*Attorney, Agent, or Firm*—Heslin & Rothenberg, P.C.

[57] ABSTRACT

A seed coating for enhancing the level of selenium in crops and therefore ensuring that sufficient levels of selenium are present in the resulting animal feed or foodstuff is described. The invention provides both a seed coating and method of coating a seed which provides a sufficient amount of selenium to the seed for uptake by the plants to produce selenium sufficient crops. The seed coating and method ensures that the selenium remains adhered to the seed in uniform, consistent amounts and which further imparts abrasion-resistance to the seed in order to reduce the toxicity risk of handling selenium-coated seeds. A suitable polymer material is also selected from the large number of polymers available in the art. A suitable polymer will mix well with the selenium material and will preferable form a dust-free film upon drying.

35 Claims, 4 Drawing Sheets

Seed Coating for Enhancement of Se
Silage Corn 1991

Seed Coating for Enhancement of Se
Silage Corn 1992

Seed Coating for Enhancement of Se
Silage Corn 1993

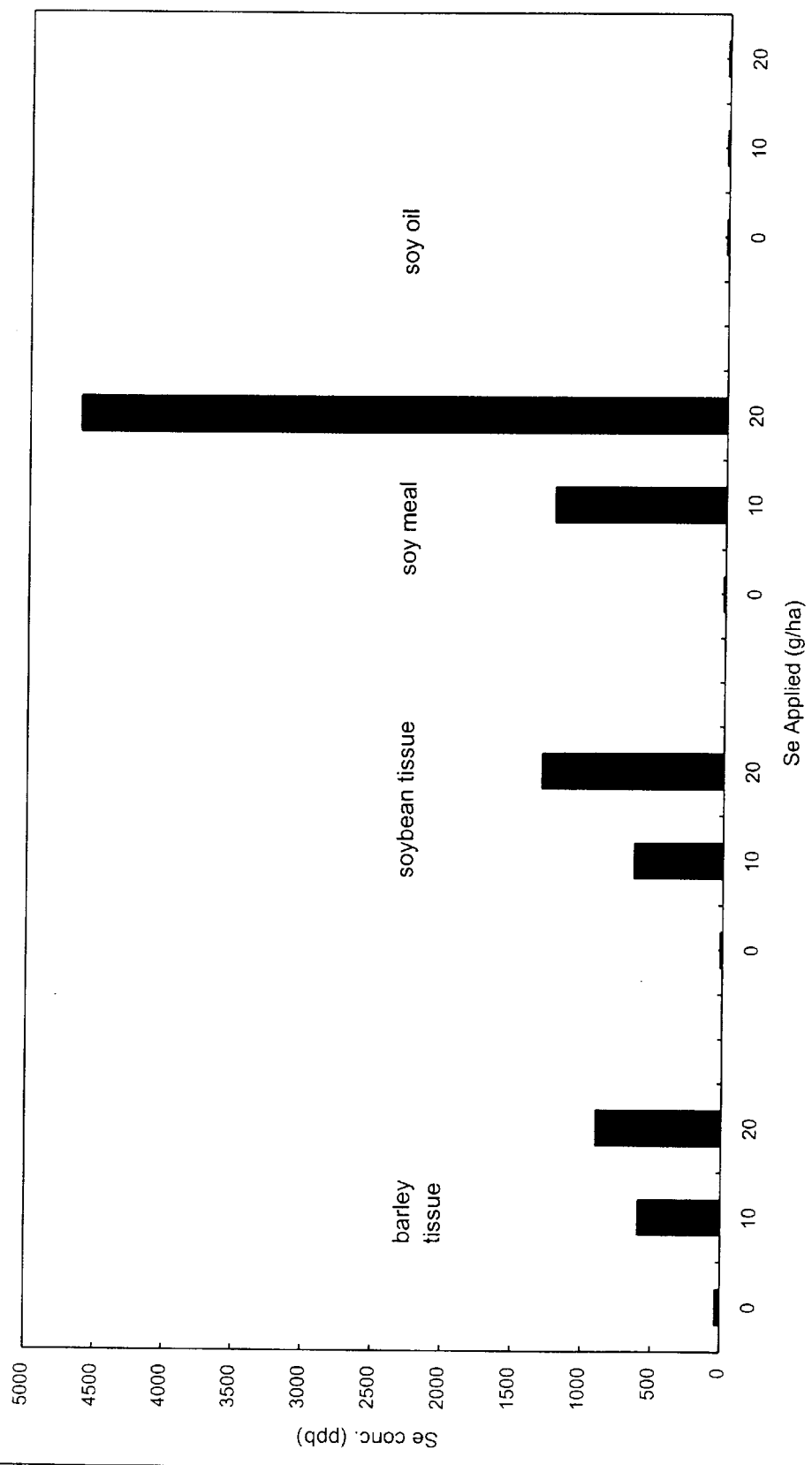
Figure 4. Se uptake by barley & soybean in B.C.

SEED COATING FOR ENHANCING THE LEVEL OF SELENIUM IN CROPS

This application is a continuation-in-part of Ser. No. 08/555,758, filed Sep. 11, 1995, abandoned.

FIELD OF THE INVENTION

The present invention relates to a seed coating for enhancing the level of selenium in crops. The invention provides a seed coating, a method of coating a seed, which provides a sufficient amount of selenium to the seed for uptake, and a coated seed.

BACKGROUND OF THE INVENTION

Large areas of North America, western Europe and Australia/New Zealand produce crops that are deficient in selenium, copper and other essential trace elements. The absence or deficiency of these trace elements affects the overall food chain, resulting in plants, and ultimately animals, deficient in these minerals. Significant deficiencies in any or a combination of specific trace elements will affect the overall health of many animals and may lead to a variety of acute health problems. Accordingly, a correct balance of trace elements is required for optimal health and livestock production. In particular, selenium is a trace element required by animals for a variety of biological processes. It is essential that animals receive appropriate levels of selenium. In all classes of livestock (dairy, beef, swine and poultry) selenium deficiency causes a variety of chronic and acute health problems.

Numerous animal nutritionists have worked on the problem of selenium deficiency in animals for years. While crops are not in themselves affected by low levels of selenium in the soil, the use of crops containing almost no selenium as animal fodder or feedstuffs leads to selenium deficiencies in all classes of animals, including humans.

Numerous methods have evolved to address the problem of selenium deficiency, which have certain problems and limitations associated with them.

Selenium is routinely provided to livestock in mineral blocks (referred to as free choice), injections and/or as mineral supplements mixed with feed.

With free choice supplements, the amount of selenium each animal intakes is not controllable and varies widely because some animals over self-administer and others under self-administer. Therefore, some of the herd/flock receive inadequate amounts and others excessive amounts of selenium (Hemingway, R. G. 1982).

Injections of selenium are time consuming, costly, need to be repeated, and involve additional handling of animals which is dangerous to the handler and stressful to the animal.

Using off-farm premixed feeds containing selenium is often not appropriate since many farmers use mostly home-grown feed and do not purchase feed from suppliers. These farmers would have to mix selenium into their farm-grown feed, which is problematic since many farms lack suitable mixing facilities and handling selenium is potentially dangerous. In cases where pre-mixed concentrated feeds are purchased, the amount of selenium required and the amount of concentrated feed used varies with each farm.

Thus, custom selenium supplementation for each farm may be required, adding to the complexity. These variables coupled with the fact that additional handling of the feed at the feed plant would be required to mix in the selenium would make the pre-mixed concentrate feeds more expensive. Therefore, pre-mixed feeds are not an ideal solution to the selenium deficiency problem.

There are a significant number of hectares of corn and other fodder crops grown in selenium deficient areas. Corn is the most important feed grain in the United States for all classes of livestock because of its high quality and high yields. Silage corn is grown as whole crop feeds on many dairy and beef farms. Corn and cereal silage are produced in Canada. Farm grown corn, pulse crops and cereal grains are also important feeds for the swine and poultry industry.

Several corn growing areas are generally deficient in selenium including, for example, Maritime provinces, Quebec, Ontario, parts of British Columbia, New England, Illinois, Indiana, Michigan, New York, North Carolina, Ohio, Pennsylvania and Wisconsin. These areas are also important dairy producers. In cooler areas, cereals replace corn in selenium deficient areas.

While it has been shown experimentally that selenium can be effectively applied by spraying a selenium solution onto plants (Gupta et al 1988), this practice is not in commercial use in view of the numerous limitations associated with plant spraying. In particular, spraying plant foliage with a selenium solution is inconvenient because it requires an additional pass over the field with a carefully prepared solution and expensive calibrated spraying equipment. Timing of the spraying is very important; spraying cannot be done in windy weather and rain will wash off the spray. Also plants must be at a sufficiently advanced growth stage to ensure uptake but applying at a stage of over advanced growth will result in mechanical damage to the crop from the tractor and application equipment.

The only commercial method now in use anywhere in the world for enhancing selenium in crops grown on selenium deficient soils is by application of a slow-release prilled selenium fertilizer on grasslands usually by aircraft. Selenium applied to the soil in this way is taken up less efficiently than selenium delivered via the seed coating method. This method is used primarily in Australia and New Zealand and has rarely been used in North America to date on a commercial scale.

Application of selenium as a fertilizer is impractical for the following reasons:

i) the selenium fertilizer would have to be in a prilled form since powdered selenium does not have the physical characteristics required for proper handling and blending, ii) prilled selenium fertilizer cannot be applied with conventional farm equipment because the application rates are far too low. That is, conventional farm equipment cannot be slowed down or regulated enough to accurately apply the selenium with the high degree of accuracy that is required. The lowest rate of fertilizer this equipment can accurately apply is 20 kg/ha whereas prilled selenium fertilizer must be applied at a rate of 1 kg/ha, iii) blending selenium with other fertilizers requires the use of prilled selenium fertilizer;

iv) it is practically impossible for a farmer to blend prilled selenium with other fertilizer on their farm since this requires the proper mixing equipment (which farmers do not have) to ensure that exact minute amounts of selenium are uniformly blended throughout large volumes of fertilizers;

v) the only forms of prilled selenium fertilizer that are currently commercially available are slow-release which is unsuitable for certain plants such as corn since the selenium is not rapidly available in the soil;

vi) the blending process is potentially dangerous to the farmer because of the physical handling and the potential of inhaling air-borne selenium dust or the potential of skin contact or absorption of the selenium dust;

vii) applying selenium blended with fertilizer is impractical because all fields require different amounts and types of fertilizer which would require custom blending for every field which would be difficult and expensive;

viii) blending the prilled selenium with an inert dilutant (eg vermiculite) would add to the cost to fertilize the field.

There has been a need to deliver selenium to crops via a seed coating technology that overcomes the aforementioned limitations and other problems associated with delivering the selenium with fertilizers.

Seeding rates for individual crops are relatively uniform over wide geographic areas, usually varying by less than 20% in contrast to fertilizer rates which vary greatly (0–500 kg/ha of product). Delivering selenium to the crop via the seed, rather than fertilizer, is better since a controlled level of selenium in the seed coat provides a more predictable and optimal amount of selenium in any given crop. Further, it is easier for the farmer to assess whether the correct amount of selenium has been applied as rate of application is related to emerging plant population which can be checked visibly. Such checks cannot be done with fertilizer application rates. Further, fertilizer is not suitable to deliver selenium because fertilizer needs vary so significantly from field to field and crop to crop.

Custom blending selenium whether at a fertilizer plant or on a farm can easily lead to errors in selenium application rates. Low rates will lead to the health problems livestock experience with selenium deficiency and excessive rates may threaten animal health, plant health or the environment.

A coated seed simplifies these quality control issues since the exact amount of selenium applied to each seed at the seed-coating plant can be very accurately controlled.

As the exact amount of selenium can be put on each seed and the plant uptakes the selenium at a predictable and consistent rate, it is far easier to control the exact amount of selenium in the crop. Other methods do not allow for this level of control. Seed coating allows for the control, consistency and repeatability from year to year that is required for proper livestock management practices.

Accordingly, there has been a need for a technology that overcomes the aforementioned problems and limitations. Specifically, there has been a need for a technology that effectively raises selenium levels in crops in an efficient, uniform, convenient, consistent, safe manner that also allows for accurate, consistent manipulation of the level of selenium in the crop. Seed coating technology can achieve this goal. Gissel-Nielsen et al (1984) disclose the application of selenium solutions onto seeds (pages 424–425) with variable results and suggest that seed coating technologies may be used for the administration of selenium to the seed. However, no such technologies are disclosed, nor were any coated seeds produced.

In summary, there has been a need for selenium seed coating technologies that assures the farmer that his crop will contain enough selenium every year, regardless of geographical location, without additional work or inputs and that specifically address the following criteria:

1. Toxicity

Selenium is potentially toxic to both plants and animals above certain levels and, accordingly, must be handled as such.

a) Phytotoxicity

With respect to plants, the primary issue is phytotoxicity, Selenium applied directly to plants above certain levels, may result in reduced plant growth or possibly kill the plant. In the past, it has also been considered that the application of selenium directly to the seed of the plant would have a phytotoxic effect in view of the relatively high concentration of selenium immediately adjacent the new plant roots during germination. This was considered to be of particular concern especially as the levels of selenium are increased. Previous studies have shown that selenium can negatively affect seed germination and elongation of young roots in several crop species (Levine 1925, Spencer and Siegel 1978, Carlson et al. 1989). In the study by Carlson et al (1989) the length of the young roots of sorghum, which is related to corn, were reduced by concentrations of selenium of 16–32 mg/litre of solution. In another study, selenium reduced yield of sorghum by up to 95% (Carlson et al. 1991). In this trial, sodium selenate was more deleterious to sorghum than sodium selenite. Wheat and barley may be more resistant to selenium than sorghum (Carlson et al. 1989, Ylaranta 1983).

b) Human Toxicity

With respect to humans, the primary issue is the toxicity associated with the inhalation of air-borne selenium or absorption of the selenium through the skin. Past experimental seed coating techniques using selenium, such as that disclosed in Gupta et al (1983) simply involved a process where the seed shell is made sticky with gum arabic and peat moss to which a slurry of water and selenium is added. The seed was dried leaving a certain amount of selenium attached to the seed. Handling of the seed leads to two problems. The first is the loss of the selenium coat from the seed by abrasion thereby leaving an inconsistent amount of selenium on each seed resulting in inconsistent and unpredictable levels of selenium in each plant and therefore leading to unpredictable levels of selenium in the feed. The second problem is the danger of inhaling air-borne selenium produced through handling the seed or prilled fertilizer or the absorption of the selenium through the skin when workers handle the seed or prilled fertilizer.

2. Linear Rate Response and Repeatability from Year to Year

Uptake of selenium by plant roots is regulated in part at least by energy requiring processes (Arvy 1993). Accordingly, the efficiency of selenium uptake depends on the energy status of the plant and growing conditions would be expected to affect selenium content. Selenium uptake is also affected by sulphur content of the soil. Some plant species are adapted to actively exclude selenium (Wu and Huang 1992). Based on these factors, the rate of uptake should vary within the year and from year to year. Indeed, Gupta and Macleod (1994) reported that soybean cv. Maple Isle receiving 10 g/ha of selenium (as selenate) contained 599 ppb in 1989 and 1458 ppb in 1990 even though the two sites had similar soil characteristics. Unpredictable levels of selenium uptake by the plant may lead to either deficient or toxic levels of selenium in the animal feed. Therefore, any commercially acceptable solution to the selenium deficiency problem has to overcome this as good livestock management practices requires that a farmer can accurately and consistently control the amount of selenium in the feed from year to year.

3. Efficient Uptake

Recovery rates for selenium applied (as selenate) to barley in the soil was at a rate of 4–10% (Ylaranta 1983). Similar rates of uptake efficiency occur with wheat utilizing a variety of application methods (Stephen et al 1989). It has been demonstrated that corn takes up about 5% of soil supplied selenium. Commercial available prilled selenium designed for slow release, has been shown to be taken up with even less efficiency, Accordingly, a technology is required to improve the uptake efficiency of selenium to reduce loss and risk of contamination to the environment.

4. Distribution of Selenium in the Plant

Corn is fed to ruminant animals either as a whole plant or as grain whereas non-ruminants, such as pigs and fowl, use only the grain portion of the corn or other crops. Thus for monograstrics it is important that the selenium is translocated to the cobs and not just stored in the leaves. Previous work has shown a greater concentration of selenium in the grain compared to straw in barley and soybeans (Ylaranta 1983, Gupta and Macleod 1994, Carey and Allaway 1973). Uptake of selenium from a seed coat was expected to be more rapid than soil applied selenium because of the proximity of the new roots to the selenium. Since selenate is rapidly absorbed and translocated in the plant, it was expected that most of the selenate would be quickly stored in the young leaves.

5. Optimum Selenium Formulation

It is known that particular forms of selenium do not work on particular plants. For example, selenium, as barium selenate, is not effective with corn in its uptake whereas for grass, uptake is effective. Accordingly, an optimal selenium formulation is required to ensure efficient uptake.

6. Uniform Application on Seed

Uneven application of selenium to seed results in some plants receiving greater selenium rates than others. Accordingly, because selenium is potentially phytotoxic, uniform application of selenium to each seed is necessary to avoid some seeds receiving toxic levels of selenium.

In view of the problems of producing selenium enhanced plants without the associated risk of plant, human or animal toxicity, there has been a need for a convenient, effective method for addressing the problems associated with livestock production in selenium deficient areas. Specifically, there has been a need for a convenient, effective method of ensuring plant uptake of selenium to produce plants which provide the required levels of selenium in animal feed in a consistent, reliable manner to enhance livestock vitality while ensuring that the plants, animals and handlers are not subjected to toxic levels of selenium.

Furthermore, there has also been a need for a method of supplying selenium to animals through the animal feed in order to eliminate the need for secondary treatment of the animals (injections) while ensuring a constant and consistent supply of selenium in the animals' diet.

Furthermore and more specifically, there has been a need for a seed coating technique in which a seed is coated with a seed coating containing selenium that accurately places an exact and uniform amount of selenium on each seed and thereafter covered by a water-soluble polymer film that encapsulates the entire seed. There has also been a need for a seed coating technique where the polymer coating is sufficiently resilient to prevent dusting off so dust borne levels of selenium do not rise to toxic levels during normal handling of the seed and to prevent each seed from ending up with non-uniform amount of selenium before planting. There has also been a need for a seed coating technique where a nutrient, fungicide and/or biocide coat may be optionally provided between the seed treatment coat and the polymer film to enhance the early growth of the seed. There has also been a need for coated seeds which improve the flow of seeds during handling.

Seeds of certain crops, such as corn, are routinely treated with fungicides. Accordingly, there has also been a need for a selenium seed-coating technology that incorporates fungicides into the seed coats wherein the seed coats also provide a protective layer thus rendering the fungicide/selenium treated seed safer to handle.

Past seed coating techniques have generally addressed the problems associated with improving the growth of plants and have not addressed the problem of enhancing animal fodder. Examples of soil and seed coating or treatment techniques are found in the prior art. For example, U.S. Pat. No. 4,735,015 discloses a seed protective coating using a film forming composition comprising polyoxyethylene-polyoxybutylene block co-polymers for controlling water uptake by the seed.

U.S. Pat. No. 3,911,183 discloses a seed coating process in which a seed is coated with polymer-pesticide film. Halogenated vinyl resin is used as a film former and pesticide carrier.

U.S. Pat. No. 3,698,133 discloses a plant seed with a multiple coating. The coating is in two layers, an inner porous coating permeable to water and an outer coating of a polymer with a controlled permeability to water. This patent discloses the use of additives to enhance particular functions of the plant.

U.S. Pat. No. 4,735,017 discloses a coated seed having inorganic additives in the coating.

U.S. Pat. No. 5,017,374 discloses a seed dressing which affords trace elements, such as Zn and Cr to livestock by plant uptake from the coated seeds using fungal spores.

U.S. Pat. No. 5,044,116 discloses a method for polymer coating of seed, which coating may include additives.

U.S. Pat. No. 4,229,613 discloses compositions for the controlled release of trace nutrients into soil including selenium.

Canadian Patent Application 2,042,661 discloses a selenium composition for application to soil and pastures. The composition includes barium selenate in a slow release form and water-soluble selenium compound.

U.S. Pat. No. 4,388,303 discloses the use of selenium (as selenite absorbed soil) in a plant for repelling foragers by inducing nausea.

U.S. Pat. No. 4,656,083 discloses the conversion of selenium metal to odiferous dimethyl selenide by soil bearing selenium-metabolizing organisms for repelling foragers.

U.S. Pat. Nos. 4,847,087 and 5,169,647 disclose adding selenium from selenium-in-sulfur compositions to soil for plant uptake so that ruminant animals may receive nutrient selenium.

U.S. Pat. No. 4,880,628 discloses a sustained release composition for livestock having a trace element, for example selenium, in a slowly soluble cement.

U.S. Pat. No. 4,251,952 discloses the use of water-insoluble polymeric materials blended with sugar for coating seeds. Although there is suggestion within this application that such seed-coating compositions may be used for the application of a range of compounds, including micronutrients, the use of selenium was not disclosed or contemplated in any manner. Furthermore, the present invention is directed to the use of water-soluble polymers v. insoluble polymers.

During development of a selenium-coated seed it was observed that many commercially available polymers are not compatible with selenium. The addition of selenium to the polymeric materials lead to coagulation or precipitation, or the selenium-polymer mixture was generally immiscible. Following screening of many water-soluble polymeric materials, several classes of polymers were found to be compatible with selenium and useful for application of high rates of selenium to seeds.

SUMMARY OF THE INVENTION

The present invention relates to a seed coating for enhancing the level of selenium in crops. The invention provides a water-soluble seed coating, a method of coating a seed, which provides a sufficient amount of selenium to the seed for uptake, and a coated seed.

In accordance with the invention, a seed coating for enhancing selenium uptake into a plant is provided comprising an abrasion-resistant, water-soluble seed coating material within which selenium is soluble, and a sufficient amount of a selenium-containing compound, sufficient to yield a nutritionally required amount of selenium in said plant. Preferably the plants are crop plants such as a pulse crop, a cereal crop, a large grain crop, a grass crop, and other broad leaf crops or the like.

The present invention is further directed to a coated seed for enhancing selenium uptake into a plant comprising a seed and a seed coating composition comprising an abrasion-resistant, water-soluble seed coating material within which selenium is soluble, and a sufficient amount of a selenium-containing compound, sufficient to yield a nutritionally required amount of selenium in said plant.

The choice of abrasion-resistant, water-soluble seed coating material, according to the present invention, preferably must mix well with the selenium-containing compound and preferably must together form a stable dust-free film after drying.

In one embodiment of the present invention there is provided a coated seed for enhancing selenium uptake into a plant comprising a seed and a seed coating composition comprising an abrasion-resistant, water-soluble seed coating polyvinyl acetate homopolymer emulsion material and a sufficient amount of a selenium-containing compound, sufficient to yield 100 to 300 ng of selenium per gram dry weight of said plant.

The present invention is also directed to a method of coating seeds for enhancing selenium uptake into plants comprising the steps of:

a) solubilizing a selenium-containing compound in water to form an aqueous selenium solution;

b) mixing the aqueous selenium solution with a water-soluble polymer emulsion to form a polymer/selenium solution;

c) mixing the polymer/selenium solution with a sufficient quantity of seeds to form a film coat on the seeds;

d) curing the seeds from step c) to form an abrasion-resistant protective coating on the seeds.

BRIEF DESCRIPTION OF THE DRAWINGS

These and other features of the invention will be more apparent from the following description in which reference is made to the appended drawings wherein:

FIG. 4 is a graph showing the relationship between selenium application rate and concentration of selenium in barley and soybean tissues, as well as in oil extracted from soybeans.

DETAILED DESCRIPTION OF THE INVENTION

Figure 1:
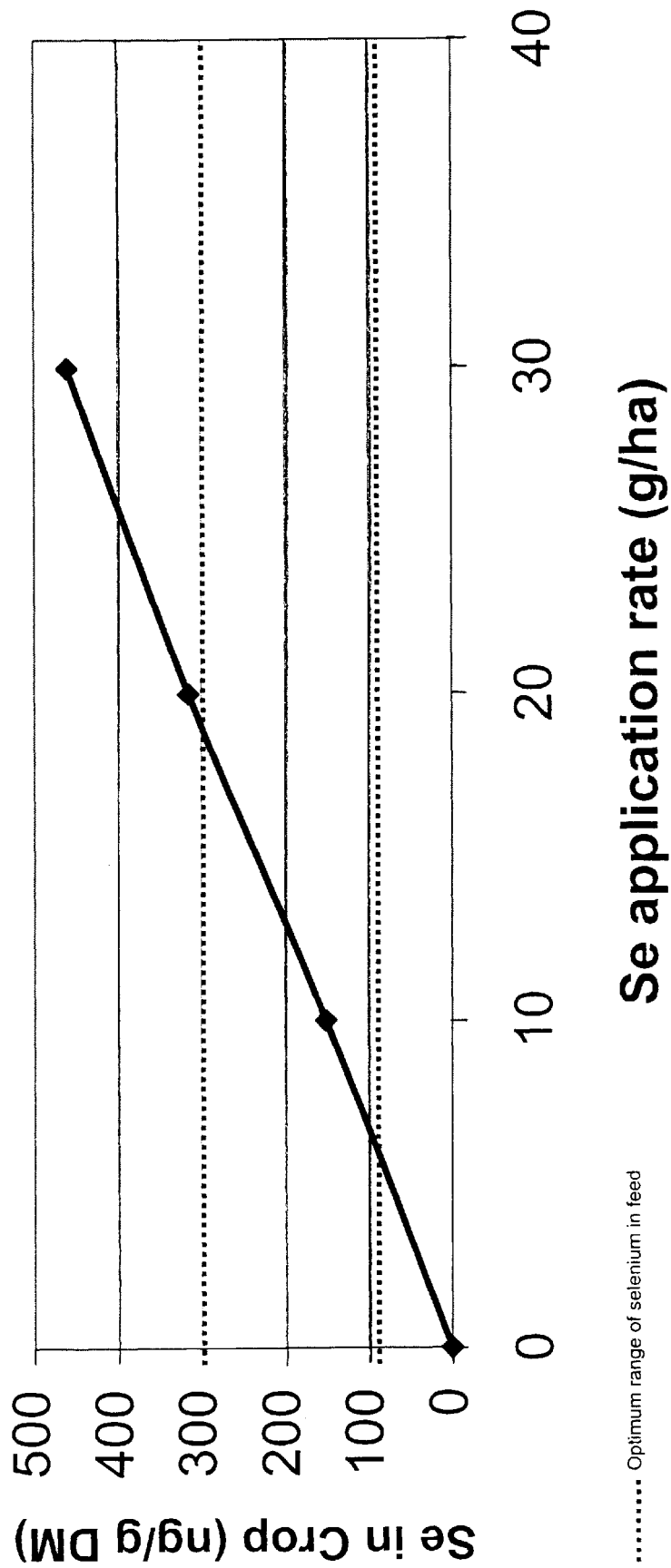
FIG. 1 is a graph showing the linear relationship between the level of selenium in a seed coat of a coated seed and the selenium content in whole corn grown from the coated seed for a 1991 test plot.

In accordance with the invention, a seed-coating technology is provided which meets the requirements of a selenium-coated seed as set forth above, namely:

1) being non-phytotoxic to the growth of the plant and reducing the toxic risk to handlers of the seeds;

2) having a linear and reliable rate response with respect to uptake over the full range of selenium application rates and repeatability from year to year;

3) providing a uniform coating on each seed to ensure consistency between plants, resulting in an effective distribution of selenium within a number of plants;

4) providing an optimum formulation that ensures an efficient uptake of the selenium without wasting or losing selenium to the environment.

In accordance with the present invention, a seed coating incorporating a sufficient amount of a selenium-containing compound was developed. Said seed coating, when applied to a seed, facilitates an enhanced selenium uptake into the plants which develops from said seed.

The amount of the selenium-containing compound which is added to the seed coating material is an amount sufficient to yield a nutritionally required amount of selenium in the resulting plant. The nutritionally required amount of selenium in said resulting plant can range from any amount which is an increase in the plant to, but not including, an amount which would be deleterious or toxic to the animal upon eating said plant. In general, the target level for selenium in the feed depends on the overall feeding program and safe levels legislated in various countries. Thus, the nutritionally required amount of selenium to which the present invention is directed, can range from 100–400 parts per billion (ppb) (100–400 ng per gram dry weight of said plant), In a further embodiment of the present invention, the nutritionally required amount of selenium in said plant ranges from 100–300 ppb.

The sufficient amount of the selenium-containing compound which is added to the seed coating material in order to yield the nutritionally required amount of selenium in said plants is based on a number of variables. These variables include for example the selenium-containing compound; the seed size; and the number of seeds sown per hectare.

The selenium-containing compound can be almost any selenium compound, for example salts or oxides of selenium. Typical selenium compounds can include sodium selenate, sodium selenite, selenium disulphide, selenium dioxide, selenium sulfur oxide, barium selenate, potassium selenate, potassium selenite, calcium selenate, calcium selenite, and the like.

In one embodiment of the present invention, the selenium-containing compound is selected from sodium selenate, sodium selenite and selenium disulphide.

The absorption ability, or uptake of selenium by the plant will vary from one selenium-containing compound to another. Thus, it will be obvious to persons skilled in the art that if a compound is selected which has a lower absorption ability, then a higher concentration of that selenium-containing compound would be required in the coating composition to yield the nutritionally required amount of selenium in the plant, as defined above.

As by way of an example, in one embodiment of the present invention, sodium selenate is used as the selenium-containing compound. In this example, the sodium selenate is added to the seed coating composition, so that the final amount of selenium in the soil is between 5 and 50 grams of selenium per hectare.

The amount of selenium-containing compound added to the seed coating material will also vary, as noted above, depending upon the size of the seed and the seed sowing rate. For example, if a high number of seed per hectare is planted, then the amount of selenium-containing compound in the coating composition would be less than for a crop which has a lower seeding rate. The sowing rate for any particular crop would remain constant. For example the sowing rate for corn is approximately 75,000 seeds per hectare. Thus, if, when sodium selenate is used as the selenium-containing compound, the amount of selenium in the coating composition for corn would range from 5 to 50 grams per 75,000 seeds or between 5 and 50 grams of selenium per hectare. Similarly, selenium is applied to seeds of other crops, such as barley or soybean, so that the final rate of selenium application results in the desired amount of micronutrient on a per hectare basis.

In one embodiment of the present invention, where corn is the seed which is coated, and sodium selenate is the selenium-containing compound, to obtain 300 ppb concentration of selenium in the corn plant, 15 to 25 grams of selenium should be added to the seed coat material per 75,000 seeds, and more specifically 16 to 21 grams.

The present invention is directed to a selenium-containing seed coating composition, which, when said seed coating composition is applied to a seed, will yield a plant with a higher level of selenium. The present invention is directed to a seed coating composition for any type of seed, wherein said resulting plant or part thereof, is used for livestock feed or for human consumption. There is no limitation on the type of seeds which can be used according to the present invention. For example, the present invention is directed to a seed coat composition which can be used to coat seeds for the production of pulse crops, cereal crops, large grain crops, grass crops and other broad leaf crops and the like, destined for animal or human consumption.

According to the present invention, either the grain of the plant, or the whole plant, can be used as a feed source. There may be some variation between the amount of selenium which is present in the grain as compared to the whole plant. Thus, if it is known that only the grain or the seed of the crop is used as a food source, the amount of selenium-containing material used in the coating composition may require adjustment. In all cases, however, the factors discussed above will be selected to ensure that the resulting plant, or plant part, which is used as a feedstuff contains a nutritionally required amount of selenium.

The choice of abrasion-resistant seed coating material, according to the present invention, preferably must mix well with the selenium-containing compound and preferably must together form a stable dust-free film after drying. There are a number of polymer coating compositions which have been described in the prior art. However, it has been found that not all of these materials and methods can be used according to the present invention.

Polyvinyl acetate resin/dextrin blend homopolymers blended well with the selenium-containing compound at low and high concentrations of selenium. Vinyl acetate/ethylene copolymer, polyvinyl pyrrolidone homopolymer and technical protein collid do not blend as well and form brittle, dusty films, however, they may be some use at lower selenium concentrations, and be further covered by other polymeric coating materials. The polyvinyl acetate blend homopolymers are however preferred as the resulting selenate/polymer suspension formed a stable dust-free film upon drying. The method of preparing said polymers for use as seed coat material are well known in the art.

In one embodiment of the present invention, an additional abrasion-resistant coating is provided as a second outer coating. If only one coat is used, then there will be a certain amount of selenium on the outside of the coating composition and, thus, the seed will still be hazardous to handle. A second coating will form an abrasion-resistant protective coating on the seeds which will completely encase the selenium inner coat and, thus, will render the seed safer for handling purposes. Any of the polymer materials which have been described for the inner coat could be used for the outer coat material.

The seed coating can also contain other materials which are required or will enhance the germination or growth of the seed. These further materials can include nutrients such as potassium, phosphate or nitrogen, biological nutrients, or a biocide including fungicides.

In the example where a two-layered seed coating is used, a drying agent may be added to the seeds once the first seed coat has been applied to ensure water removal from the inner selenium coat to enhance the storage of the seeds. Any suitable drying agent known in the art can be used for this purpose. For example, a suitable drying agent such as calcium carbonate, calcium oxide, calcium hydroxide, vermiculite, diatomaceous earth, gypsum, talcum, bentonite, kaolin, and various metal silicates can be used.

Any seed coating method can be used according to the present invention. In general, abrasion-resistant selenium-coated seeds are prepared by first dissolving the selenium-containing material in water to form a water-selenium solution containing a known amount of selenium. The solution is then mixed with a liquid polymer emulsion to form a polymer/selenium solution. A quantity of seeds are then mixed with the polymer/selenium solution to form a film coat on the seeds. The seeds are then cured to form an abrasion-resistant coating on the outer surface of said seeds.

As described above, in one embodiment of the present invention, an additional abrasion-resistant coating is provided on the seeds to protect the handler from the selenium coating material. In this embodiment, the seeds, after being coated with the polymer/selenium solution, are partially cured and may be mixed with a drying agent, as described above, to form a drying agent coat on the seeds. The drying agent coat may be used to ensure water removal from the inner selenium coat to enhance the storage of the seeds. The seeds are then mixed with a second liquid polymer emulsion to form an abrasive-resistant protective coating on the seeds. The seeds are then cured, While this invention is described in detail with particular reference to preferred embodiments thereof, said embodiments are offered to illustrate but not to limit the invention.

EXAMPLES

Example 1

Polymer screening for Sodium Selenate Comparability

A variety of water soluble polymers were first prepared in a standard manner to be used for seed coating which involved adjusting the viscosity and percent solids by dilution with water. In the case of a powdered formulation, the polymer was prepared according to the manufactures directions by suspending in hot water and allowing it to cool to room temperature. A liquid dye was then added to the polymer. An aqueous solution of sodium selenate was prepared by dissolving sodium selenate (anhydrous) in water. This solution was then added to the polymer to be screened, while stirring.

The following water-soluble polymer types were used:
Type
A) Synthetic polymers
1. Latex polymer
2. Vinyl acetate/ethylene copolymer
3. Polyvinyl acetate resin/dextrin blend homopolymer
4. Polyvinyl alcohol
5. Polyvinyl pyrrolidone homoplymer
6. Polyvinyl acetate homopolymer emulsion
7. Vinyl pyrrolidone vinyl acetate copolymer
B) Natural Polymers
8. Technical protein colloid These polymers were obtained from the following manufactures:CelPril Inc; ISP Inc.; Reichold Chemicals; and Chang Chun Petrochemicals Co. Ltd.

The liquid dye and sodium selenate which was used is shown below:
1. Red Diazo Dye
2. Sodium selenate, anhydrous The method of preparing the sodium selenate/polymer solutions are described below (the "Test" number corresponds to the number of the polymer given above).

Test 1

Prepare a 18.4% (w/v) aqueous sodium selenate solution using $Na_2SeO_4$, anhydrous in deionized $H_2O$ at 21° C. Add 37 ml sodium selenate solution to 12.0 ml latex polymer to which 1.0 ml Red Diazo Dye has been added. Stir with a glass rod. Final sodium selenate concentration 13.6% (w/v). Prepare a film by adding 5.0 ml of the suspension to a 100 ml disposable petri dish.

Test 2

Prepare a 48.6% (w/v) aqueous sodium selenate-e solution using $Na_2SeO_4$, anhydrous in deionized $H_2O$ at 21° C. Add 14 ml sodium selenate solution to 36.0 ml vinyl acetate/ethylene copolymer to which 1.0 ml Red Diazo Dye has been added. Stir with a glass rod. Final sodium selenate concentration 13.3% (w/v). Prepare a film by adding 5.0 ml of the suspension to a 100 ml disposable petri dish.

Test 3

Prepare a 48.6% (w/v) aqueous sodium selenate solution using $Na_2SeO_4$, anhydrous in deionized $H_2O$ at 21° C. Add 14 ml sodium selenate solution to 36.0 ml polyvinyl acetate resin/dextrin blend homopolymer to which 1.0 ml Red Diazo Dye has been added. Stir with a glass rod. Final sodium selenate concentration 13.3 % (w/v). Prepare a film by adding 5.0 ml of the suspension to a 100 ml disposable petri dish.

Test 4

Prepare a 10% w/v solution of polyvinyl alcohol according to manufacturers directions as well as a 45% (w/v) aqueous sodium selenate solution using $Na_2SeO_4$, anhydrous in deionized $H_2O$ at 21° C.:
i) for a 13.5% (w/v) final sodium selenate concentration add 1.5 ml sodium selenate solution to 2.5 ml of the above polymer at 21° C., and add 1.0 ml deionized $H_2O$;
ii) for a 7.9% (w/v) final sodium selenate concentration add 0.75 ml sodium selenate solution to 2.5 ml of the above polymer at 21° C., and add 1.75 ml deionized $H_2O$.

Mix using a Vortex mixer. Prepare a film by adding 5.0 ml of the suspension to a 100 ml disposable petri dish.

Test 5

Prepare a 45% (w/v) aqueous sodium selenate solution using Na2SeO4, anhydrous in deionized $H_2O$ at 21° C.:
i) for a 13.5% (w/v) final sodium selenate concentration add 1.5 ml sodium selenate solution to 1.65 ml of polyvinyl pyrrolidone homopolymer, and add 1.85 ml deionized $H_2O$;
ii) for a 7.9% (w/v) final sodium selenate concentration add 0.75 ml sodium selenate solution to 1.65 ml polyvinyl pyrrolidone homopolymer, and add 2.8 ml deionized $H_2O$.

Mix using a Vortex mixer. Prepare a film by adding 5.0 ml of the suspension to a 100 ml disposable petri dish.

Test 6

Prepare a 45% (w/v) aqueous sodium selenate solution using $Na_2SeO_4$, anhydrous in deionized $H_2O$ at 21° C.
i) for a 13.5% (w/v) final sodium selenate concentration add 1.5 ml sodium selenate solution to 3.5 ml polyvinyl acetate homopolymer emulsion;
ii) for a 7.9% (w/v) final sodium selenate concentration add 0.75 ml sodium selenate solution to 3.5 ml polyvinyl acetate homopolymer emulsion, and add 0.75 ml deionized $H_2O$.

Mix using a Vortex mixer.

Test 7

Prepare a 45% (w/v) aqueous sodium selenate solution using $Na_2SeO_4$, anhydrous in deionized $H_2O$ at 21° C.:
i) for a 13.5% (w/v) final sodium selenate concentration add 1.5 ml sodium selenate solution to 3.5 ml vinyl pyrrolidone vinyl acetate copolymer;
ii) for a 7.9% (w/v) final sodium selenate concentration add 0.75 ml sodium selenate solution to 3.5 ml vinyl pyrrolidone vinyl acetate copolymer, and add 0.75 ml deionized $H_2O$.

Mix using a Vortex mixer.

Test 8

Prepare a 45% (w/v) aqueous sodium selenate solution using $Na_2SeO_4$, anhydrous in deionized $H_2O$ at 21° C.:
i) for a 13.5% (w/v) final sodium selenate concentration add 1.5 ml sodium selenate solution to 3.5 ml technical protein colloid;
ii) for a 7.9% (w/v) final sodium selenate concentration add 0.75 ml sodium selenate solution to 3.5 ml technical protein colloid, and add 0.75 ml deionized $H_2O$.

Mix using a Vortex mixer. Prepare a film by adding 5.0 ml of the suspension to a 100 ml disposable petri dish.

The latex polymer (1) did not mix well upon addition of selenium. The suspension coagulated. Similarly, the polyvinyl alcohol polymer (4) did not mix well upon addition of selenium and the suspension also coagulated. The addition of selenium to polyvinyl acetate homopolymer emulsion (6) resulted in the suspension coagulating immediately upon addition of the selenium solution. This was true at both selenium concentrations. The vinyl pyrrolidone vinyl acetate copolymer (7) formed a precipitate immediately upon addition of the selenium solution. At lower concentrations of selenium the suspension separated into two fractions and was still not miscible.

The vinyl acetate/ethylene copolymer (2) mixed well with the selenium, however, the copolymer suspension dried to a very powdery, dusty film. Thus, if this composition were used alone, it would not be preferred as the dusty powdery film would put the seed handler at risk of exposure to selenium. It would, however, be possible to add a further polymer coat over the first coat, which would protect the handler from any selenium. The poylvinyl pyrrolidone homopolymer solution (5) was not miscible and separated. At lower concentrations the solution was soluble after vigourous mixing, however, it formed a brittle, dusty film. This polymer could be used if lower concentrations of selenium are required for seed coating.

The addition of selenium to technical protein colloid (8) resulted in the formation of a precipitate at the higher concentrations of selenium, which formed a suspension after 5 minutes. At lower concentrations a suspension was formed and the solutions mixed immediately. This composition resulted in a crystalline, some what dusty film Again this polymer could be used for the application of low concentrations of selenium to seeds and be used under a subsequent coating material.

The preferred polymer, was a polyvinyl acetate resin/dextrin blend homopolymer (3), which mixed well with the selenium and which dried to form a stable, solid, somewhat brittle film.

Not wanting to be bound by any particular theory, it is possible that the colloidal system is responsible for whether or not the polymer will coagulate when something is added to it. In the case of sodium selenate, it is possible that the anion destabilizes the system. Destabilization may be more prevalent with a copolymer.

In summary out of the 8 different commercially available polymer classes tested several polymers were found to be compatible with selenium and could be used for the application of selenium to seeds. These were:

polyvinyl acetate resin/dextrin blend homopolymer, polyvinyl pyrrolidone homopolymer, and technical protein colloid.

However, out of this group only the polyvinyl acetate resin/dextrin blend homopolymer, proved compatible with higher concentrations of selenium that are required for seed coating purposes. High selenium concentrations are required since the rate of polymer application on seeds is low, from about 2–5 ml/kg, and therefore it is essential that all of the suspended selenium within the polymer be applied to the seed.

Example 2

Selenium Seed Coating on Corn Seeds

The selenium seed coating was field tested over a three year period in order to investigate the above criteria namely the phytotoxicity of selenium on the growing plant, the selenium uptake characteristics by the growing plant and the repeatability over several growing seasons in view of the seed coating techniques.

Seed of corn hybrid G4066 (Funk Hybrids) was coated with selenium using a polymer seed coat of a polyvinyl acetate resin/dextrin blend homopolymer as the seed coat material.

The selenium was added to the seed coat material at a rate of 0, 5, 10, 20 or 40 g of selenium per 75,000 seeds (equivalent to grams of selenium per hectare), in the form of sodium selenate.

The selenium-coated seeds were planted in mid-May to early June on a Monroe series soil (Eutric Eluviated Brunisol), a sandy loam soil known to be low in selenium. Prior to seeding, the field was cultivated and fertilized with 300 kg/ha of nitrogen and 70 kg/ha each of potassium and phosphorus. Lime was applied when necessary.

Weeds were controlled pre-emerge with the herbicide Atrazine (1.8 kg/ha). Weeds were also controlled by hand-weeding and post-emerce broadleaf herbicides.

The corn was planted by hand, using corn jabbers, in rows spaced 75 cm apart. Seeding was done in order of increasing selenium concentration to minimize cross-contamination. Plants within a row were spaced 18 cm apart to give a final plant population of 75,000 plants/ha.

Each plot consisted of three 1.8 meter long rows. The selenium application rates were randomized within each of four replicates to give a randomized complete block design.

Plants were harvested each year in October. Plots were harvested in order of increasing selenium rates to minimize cross-contamination. The entire centre row was harvested (whole plants), weighed, then chopped with a commercial chopping machine. A representative sample of chopped material was taken, weighed and dried to a constant weight. Drying temperature was low (40° C.) to minimize volatilization of selenium. After drying, samples were reweighed, and ground to pass through a 1 mm mesh Samples were ground in order of increasing selenium concentration to minimize cross-contamination.

Selenium analysis was performed by inductively coupled plasma mass spectroscopy (ICPMS) after sample decomposition by microwave digestion. Five ml of nitric acid and a selenium stable isotope internal standard were added to 0.5 g samples which were digested in sealed Teflon vessels using microwave power. Volatile selenium hydride was generated and the quantity of selenium determined by isotope dilution ICPMS. Accuracy of the determination was verified by use of a certified reference material. The data was analyzed statistically with SAS software using a randomized complete block model.

Figure 2:
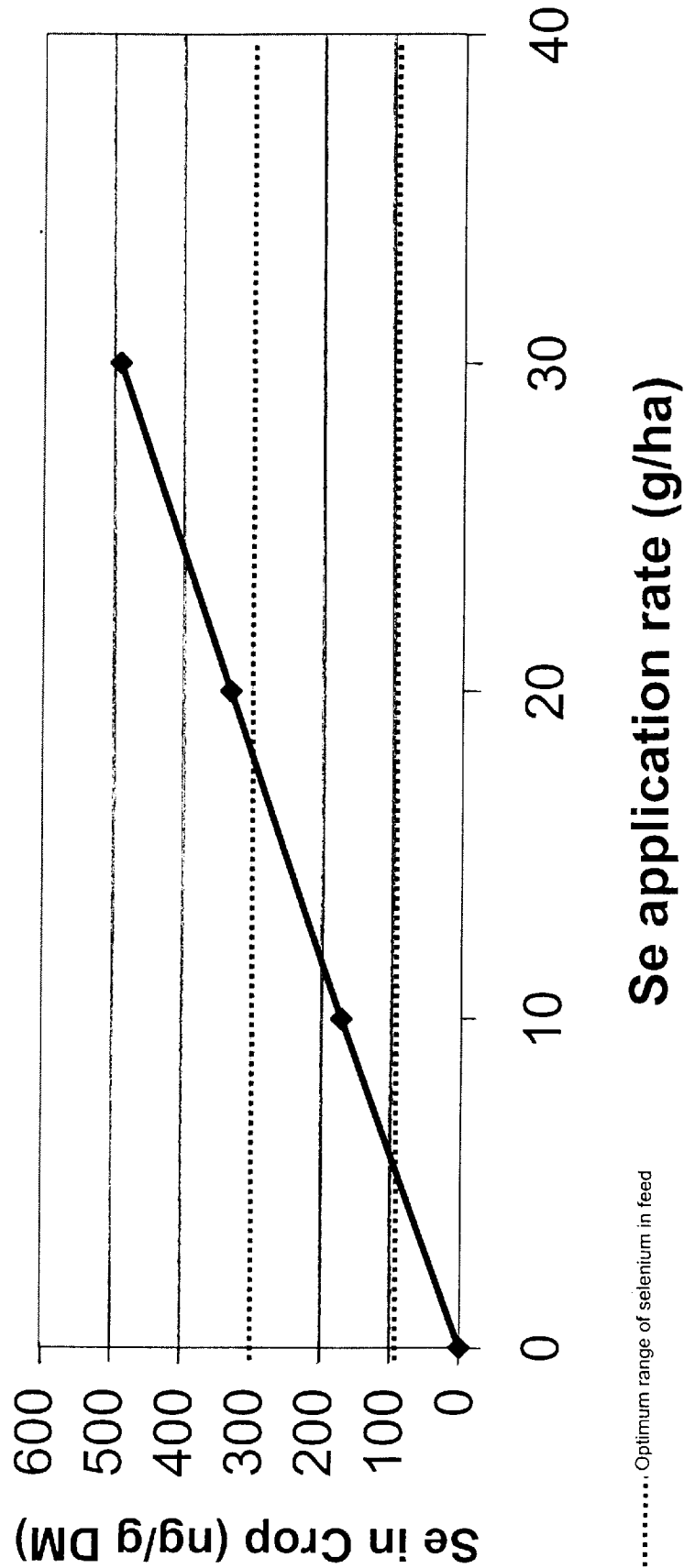
FIG. 2 is a graph showing the linear relationship between the level of selenium in a seed coat of a coated seed and the selenium content in whole corn grown from the coated seed for a 1992 test plot.
Figure 3:
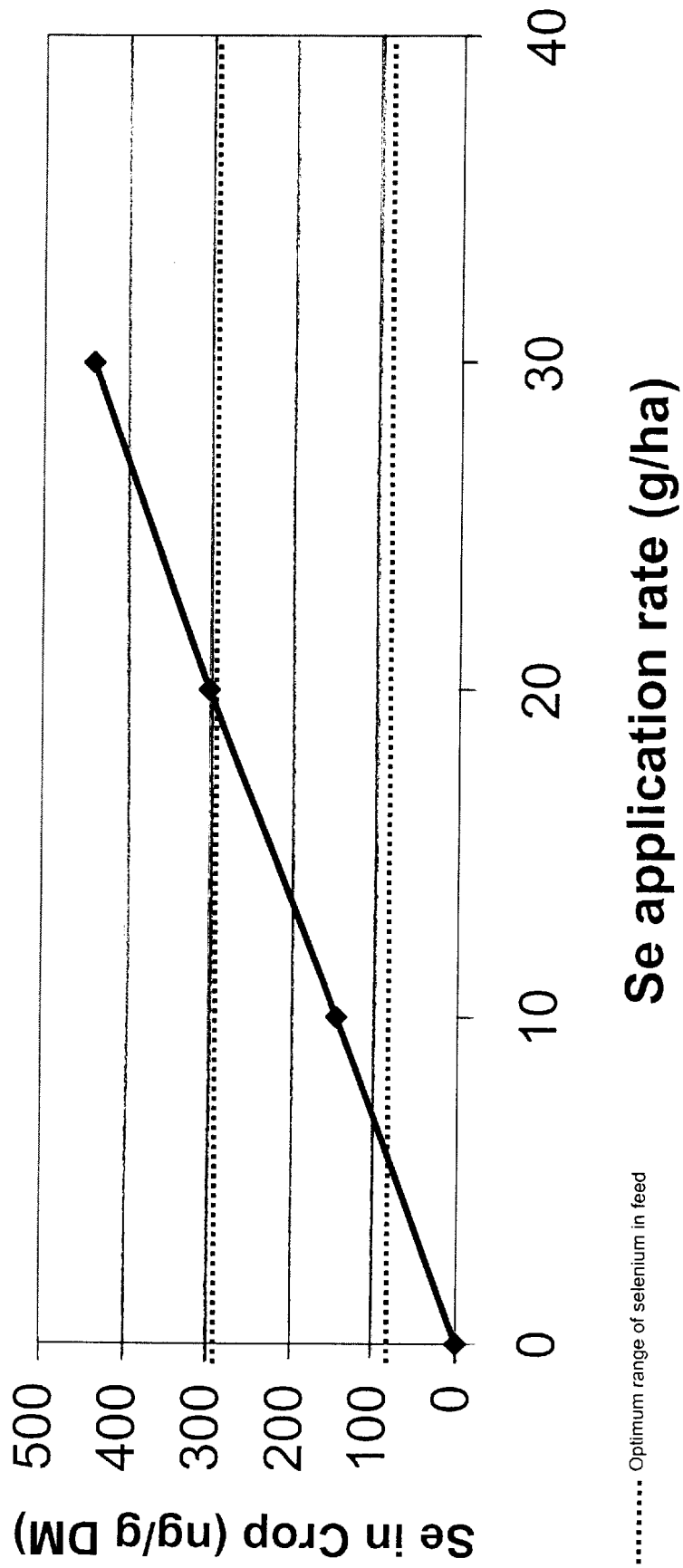
FIG. 3 is a graph showing the linear relationship between the level of selenium in a seed coat of a coated seed and the selenium content in whole corn grown from the coated seed for a 1993 test plot.

Levels of selenium in the control corn plants were approximately 2.7–9.1 ppb dry matter in the first sample. These rates are typical for crops grown in coastal British Columbia and other low selenium areas around the world. Applied selenium increased selenium content in the corn in a linear fashion in all trials (see FIGS. 1–3 and Table 1). FIGS. 1–3 and Table 1 show that for every 10 g/ha increase in application rate of selenium, as sodium selenate, selenium concentration in corn increased by 120–180 parts per billion. The target level for selenium in feed depends on the overall feeding program and safe levels legislated in various countries. To obtain 300 ppb concentration, which is commonly considered desirable, 16–21 g selenium/ha should be added to the seed coat. This corresponds to the rates of 10–20 g/ha of selenium commonly applied as fertilizer in New Zealand. Based on an average yield of 16.6 tonne/ha, the efficiency of recovery of applied selenium was in the range of 20–33%. Repeatability over the three year trial period is evident from FIGS. 1–3.

TABLE 1

Effect of selenium seed coating on yield and selenium uptake in whole crop and grain or corn in 1993

| Intended rate g/ha | Actual rate g/ha | Whole Corn | | | | Grain Se ppb |
|---|---|---|---|---|---|---|
| | | Yield t/ha | Se content ppb | Se uptake g/ha | % Se uptake | |
| 0 | 0.0044 | 18.4 | 2.7 | 0.05 | — | 6.5 |
| 0 + CACO$_3$ | 0.05 | 15.8 | 1.5 | 0.02 | — | not tested |
| 5 | 4.4 | 17.4 | 59.1 | 1.0 | 22.8 | not tested |
| 10 | 10.8 | 17.4 | 167.5 | 2.8 | 26.0 | not tested |
| 10 + CaCO$_3$ | 12.0 | 19.5 | 129.5 | 2.6 | 21.6 | not tested |

TABLE 1-continued

Effect of selenium seed coating on yield and selenium uptake in whole crop and grain or corn in 1993

| | | | Whole Corn | | | |
|---|---|---|---|---|---|---|
| Intended rate g/ha | Actual rate g/ha | Yield t/ha | Se content ppb | Se uptake g/ha | % Se uptake | Grain Se ppb |
| 20 | 18.8 | 16.5 | 288.2 | 4.7 | 25.1 | 193.0 |
| 30 | 30.7 | 16.1 | 439.0 | 6.1 | 19.9 | not tested |
| 40 | 35.6 | 11.4 | 516.9 | 7.1 | 19.9 | not tested |

Yield did not appear to be appreciably affected by selenium application except perhaps at 40 g/ha (Table 1). No visual symptoms associated with selenium applications were apparent.

The percentage of the applied selenium that was taken up by the crop ranged 20–26% and, accordingly, the percentage of uptake was not affected by selenium application rate.

Selenium concentration in the grain (193 ppb) was lower than in the whole plant (288 ppb) so for selenium enhancement of grain, 50% more selenium is required in the seed coat.

The variability of selenium content in individual plants ranged from 25% –40% of the mean (Table 2). This indicates that less than 3% of the plants contained more than 1.8 times of the desired selenium content and further, demonstrates the uniformity of the coating. This seed coating technique provides very few seeds with potentially phytotoxic levels of selenium.

TABLE 2

Variability in the selenium content of individual corn plants at 20 and 40 g Se/ha

| Plot | Rate Applied g/ha | Se content ppb | Standard deviation ppb |
|---|---|---|---|
| 1 | 20 | 277.5 | 97.5 |
| 2 | 20 | 236.0 | 82.6 |
| 3 | 20 | 251.9 | 60.5 |
| 4 | 20 | 229.8 | 64.5 |
| 5 | 40 | 470.0 | 138.0 |
| 6 | 40 | 441.8 | 81.8 |
| 7 | 40 | 678.8 | 285.1 |

Accordingly, the following general results were achieved with respect to the above criteria:

1. Toxicity

The concentrations of selenium around the corn seed coated with selenium during germination is high although difficult to quantify so the effect of the selenium seed coating on the emerging plants could not be predicted. The results show no reduction in yield to 40 g Se/ha, no reduced gemination or emergence, and no visual symptoms of stress.

2. Linear Rate Response and Repeatability

Very similar rates of uptake in the trials on three sites over 3 years was an unexpected result since growing conditions should effect selenium uptake. A linear rate would probably not occur if the seedling were damaged by the selenium.

3. Uniform Application

The results show that the application technique used was effective in supplying uniform doses of selenium to each seed (Table 2).

4. Distribution of Selenium in the Plant

Generally, the results show that the corn grain contained less selenium than the whole plant, and, hence for grain production higher rates of seed coating would be required.

5. Optimum Selenium Formulation

Other formulations of selenium (selenite, sulphide-$SeS_2$) were found to be less readily taken up from the seed coat than selenate. Neither aluminum hydroxide nor calcium carbonate enhanced the uptake of sodium selenate.

6. Uptake

The results show that selenium applied in a seed coat is absorbed at a more efficient rate of at least 20% of the quantity applied to the seed compared to other methods. It was unexpected that this seed coating technology would result in the plant uptaking selenium at more efficient rates in comparison with other methods. Thus, less selenium was wasted or lost to the environment.

Example 3

Selenium uptake by barley and soybean

Selenium was applied to barley and soybean seeds essentially as described in Example 2, and seeds planted in accordance with regular sowing procedures. Both barley and soybean were applied at 100 kg/ha and treated with selenium to provide a final rate of selenium application of 10 or 20 g/ha Plants were harvested at the end of the growing season and tissues analyzed for selenium concentrations as per Example 2.

In the case of soybean, seeds were also crushed with a Raney oilseed crusher, and the oil extracted with petroleum spirit solvent according to the standards of the American Oil Chemists Society by POS Inc (Saskatoon). The selenium concentration within samples of oil was analyzed after preparing a nitric/perchloric acid digest and adding sodium borohydride. The samples were analyzed using an atomic absorption spectrophotometer. Results are indicated in Table 3 and FIG. 4.

Levels of selenium in the control plants were relatively low for both barley or soybean, although the levels in barley were higher than that detected in soybean (13.3–63.5 Se ppb, and 9.93–22.1 Se ppb, respectively). These levels are similar to those observed in corn (Example 2). With increase selenium application, on a per hectare basis, the concentration of selenium within plant tissues increased linearly, again in agreement with that observed in corn. Levels of selenium in soybean were slightly higher than that observed in barley tissues.

It is undesirable to have a selenium contaminated oil fraction if the oil is to be used for further processing. In order to determine whether or not soybeans grown in the presence of selenium can be harvested for both meal, as well as oil, the concentration of selenium within soybean oil was examined The results from Table 3 indicate that the oil fraction of soybean, obtained from control and treated plants, was the same and below detectable limits. Therefore, growing soybean plants in the presence of selenium enables the preparation of a selenium-free oil, which can be substituted for conventionally prepared soybean oil.

TABLE 3

Selenium Concentrations within Barley and Soybean tissues

| Crop | Se rate (g/ha) | Se ppb tissue | Se pph oil | Se pph meal |
|---|---|---|---|---|
| barley | 0 | 18.7 | | |
| barley | 0 | 44.7 | | |
| barley | 0 | 63.5 | | |
| barley | 0 | 13.3 | | |
| barley | 0 | 41.6 | | |
| barley | 10 | 703 | | |
| barley | 10 | 598 | | |
| barley | 10 | 598 | | |
| barley | 10 | 476 | | |
| barley | 20 | 1010 | | |
| barley | 20 | 920 | | |
| barley | 20 | 794 | | |
| barley | 20 | 888 | | |
| soybean | 0 | 9.89 | <0.0025 | <9.95 |
| soybean | 0 | 27.2 | <0.0025 | <9.91 |
| soybean | 0 | 14.3 | <0.0025 | 27.4 |
| soybean | 0 | 9.93 | | |
| soybean | 0 | 22.1 | | |
| soybean | 10 | 561 | <0.0025 | 1110 |
| soybean | 10 | 698 | <0.0025 | 1340 |
| soybean | 10 | 521 | | |
| soybean | 10 | 778 | | |
| soybean | 20 | 1330 | <0.0025 | 4660 |
| soybean | 20 | 1420 | <0.0025 | 4600 |
| soybean | 20 | 1360 | | |
| soybean | 20 | 1100 | | |

The terms and expressions which have been employed in this specification are used as terms of description and not of limitations, and there is no intention in the use of such terms and expressions to exclude any equivalents of the features shown and described or portions thereof but it is recognized that various modifications are possible within the scope of the claims.

All scientific publications and patent documents are incorporated herein by reference.

References

Ylaranta, T. 1983 Effect of applied selenite and selenate on the selenium content of barley (*Hordeum vulgare*) Ann Agric., Fenn 22: 164–174.

Gupta, U. C. and Maleod S. A. 1994 Effect of various sources of selenium fertilizer on selenium concentration of feed crops. Can J. Soil Sci. 74: 285–290.

Gupta, U. C., MacRae, K. B. and Winter K. A. 1988 Selenium enrichment of crops through foliar applications Can J. Soil Sci. 68: 519–526.

Carlson, C. L., Kaplan D. I. and Adriano, D. C. 1989 Effect of selenium on germination and radical elongation of selected agronomic species. Environmental and Experimental Botany 27: 493–698.

Spencer N. E,. and Siegel S. M. 1978 Effect of sulk and selenium—Hg—toxicity in turnip see germinates Water Air Soil Pollut. 9: 423–427.

Levine V. E. 1925 Effect of selenium compounds upon growth and germination in plants Am J. Bot 12: 82–90.

Carlson, C. L., Adriano D. C., and Dixon P. M. 1991 Effects of soil applied selenium to growth and selenium content of a forage species. Envira Quality 20: 363–368.

Arvy M. P. 1993 Selenated and selenite uptake and translocation in bean plants (Plaseolus vulgaris). Journal of Exp. Botany 44: 1083–1087.

Wu, L. And Huang Z. Z. 1992 Selenium assimilation and nutrient element uptake in white clover and fall fescue under the influence of sulphate concentration and selenium tolerance of the plants. Journal of Exp. Bot. 43: 549–555.

Carey E. E. and Allaway W. H. 1973 Selenium content of field crops grown in selenite treated soils. Agron J. 65: 922–925.

Hemingway, R. G. 1982 Report of a Study Group Commissioned by the Scottish Agricultural Colleges and the Scottish Agricultural Research Institutes, Edinburgh. Trace Element Deficiency in Ruminants.

Gupta, U. C., Winter, K. A. and Kunelius, H. T. 1983 Effect of treating forage seed with selenium on the concentrations of alfalfa and Westerwolds ryegrass. Can J. Soil Sci. 63:641–643.

Stephen, R. C., Saville, D. J., and Watkinson J. H. 1989 The effects of sodium selenate applications on growth and selenium concentration in wheat. N. Zeal. J. Crop Hort. Sci. 17:229–237.

The embodiments of the invention in which an exclusive property or privilege is claimed are defined as follows:

1. A seed coating composition for enhancing selenium uptake into a plant comprising;
    i) a polyvinyl acetate resin/dextrin blend homopolymer; and
    ii) an amount of a selenium-containing compound, sufficient to yield a nutritionally required amount of selenium in said plant.

2. The seed coating composition of claim 1, wherein the nutritionally required amount of selenium is up to 400 ppb, based on dry weight of the plant.

3. The seed coating composition of claim 2, wherein the nutritionally required amount of selenium is from 100 to 400 ppb, based on dry weight of the plant.

4. The seed coating composition of claim 3, wherein the nutritionally required amount of selenium is from 100 to 300 ppb, based on dry weight of the plant.

5. The seed coating composition of claim 4, wherein the selenium-containing compound is selected from the group consisting of sodium selenate, sodium selenite, selenium dioxide, selenium disulphide, selenium sulfur oxide, barium selenate, potassium selenate, potassium selenite, calcium selenate and calcium selenite. like.

6. The seed coating composition of claim 5, wherein the selenium-containing compound is selected from the group consisting of sodium selenate, sodium selenite and selenium disulphide.

7. The seed coating composition of claim 6, wherein the selenium-containing compound is sodium selenate.

8. The seed coating composition of claim 7, wherein the plant is selected from the group consisting of a pulse crop, a cereal crop, a large grain crop, a grass crop, and other broad leaf crops.

9. A coated seed for enhancing selenium uptake into a plant comprising a seed and the seed coating composition of claim 1.

10. The coated seed of claim 9, wherein the nutritionally required amount of selenium is up to 400 ppb, based on dry weight of the plant.

11. The coated seed of claim 10, wherein the nutritionally required amount of selenium is from 100 to 400 ppb, based on dry weight of the plant.

12. The coated seed coating of claim 11, wherein the nutritionally required amount of selenium is from 100 to 300 ppb, based on dry weight of the plant.

13. The coated seed of claim 12, wherein the selenium-containing compound is selected from the group consisting of sodium selenate, sodium selenite, selenium dioxide, selenium disulphide, selenium sulfur oxide, barium selenate, potassium selenate, potassium selenite, calcium selenate, calcium selenite, and the like.

14. The coated seed of claim 13, wherein the selenium-containing compound is selected from the group consisting of sodium selenate, sodium selenite and selenium disulphide.

15. The coated seed of claim 14, wherein the selenium-containing compound is sodium selenate.

16. The coated seed of claim 15, wherein the plant is selected from the group consisting of a pulse crop, a cereal crop, a large grain crop, a grass crop, and other broad leaf crops.

17. The coated seed of claim 9, further comprising an abrasion-resistant polymeric outer coat which encapsulates the seed coating composition.

18. A method of coating seeds for enhancing selenium uptake into plants comprising the steps of:
   a) mixing the seed coating composition of claim 1 with a sufficient quantity of seeds to form a film coat on the seeds; and
   b) curing the seeds from step a) to form an abrasion-resistant protective coating on the seeds.

19. The method of claim 18 further comprising the step of mixing the seeds from step b) with a liquid polymer emulsion to form an abrasion-resistant polymeric outer coat on the seeds.

20. A method of preparing selenium-free oil from selenium-enriched oil-producing plants grown in the presence of selenium comprising: coating seeds of an oil-producing plant using the method of claim 18, growing the oil-producing plant, harvesting the seed, and extracting the selenium-free oil from the seed.

21. The method of claim 20, wherein the oil-producing plant is soybean.

22. The seed coating composition of claim 1 comprising up to about 13.3% (w/v) of said selenium-containing compound.

23. The seed coating composition of claim 1 comprising about 71% (v/v) of said polyvinyl acetate resin/dextrin blend homopolymer.

24. A seed coating composition for enhancing selenium uptake into a plant comprising:
   i) an abrasion-resistant water-soluble seed coating material selected from the group consisting of polyvinyl pyrrolidone homopolymer, and technical protein colloid; and
   ii) a selenium-containing compound, wherein the selenium-containing compound is present up to about 7.9% (w/v).

25. A seed coating composition for enhancing selenium uptake into a plant comprising:
   i) a vinyl acetate/ethylene copolymer; and
   ii) a selenium-containing compound, wherein the selenium-containing compound is present up to about 13.3% (w/v).

26. The seed coating composition of claim 24, wherein the selenium-containing compound is selected from the group consisting of sodium selenate, sodium selenite, selenium dioxide, selenium disulphide, selenium sulfur oxide, barium selenate, potassium selenate, potassium selenite, calcium selenate, and calcium selenite.

27. The seed coating composition of claim 23, wherein the selenium-containing compound is selected from the group consisting of sodium selenate, sodium selenite, selenium dioxide, selenium disulphide, selenium sulfur oxide, barium selenate, potassium selenate, potassium selenite, calcium selenate, and calcium selenite.

28. The seed coating composition of claim 24, wherein the plant is selected from the group consisting of a pulse crop, a cereal crop, a large grain crop, a grass crop, and other broad leaf crops.

29. The seed coating composition of claim 25, wherein the plant is selected from the group consisting of a pulse crop, a cereal crop, a large grain crop, a grass crop, and other broad leaf crops.

30. A coated seed for enhancing selenium uptake into a plant comprising: a seed, the seed coating composition of claim 24, and an abrasion-resistant polymeric outer coat.

31. A coated seed for enhancing selenium uptake into a plant comprising: a seed, the seed coating composition of claim 25, and an abrasion-resistant polymeric outer coat.

32. A method of coating seeds for enhancing selenium uptake into plants comprising the steps of:
   a) mixing the seed coating composition according to claim 24 with a sufficient quantity of seeds to form a film coat on the seeds;
   b) curing the seeds from step a); and
   c) mixing the seeds from step b) with an abrasion-resistant polymeric outer coat.

33. A method of coating seeds for enhancing selenium uptake into plants comprising the steps of:
   a) mixing the seed coating composition according to claim 25 with a sufficient quantity of seeds to form a film coat on the seeds; and
   b) curing the seeds from step a); and
   c) mixing the seeds from step b) with an abrasion-resistant polymeric outer coat.

34. A method of preparing selenium-free oil from selenium-enriched oil-producing plants grown in the presence of selenium comprising: coating seeds of an oil-producing plant using the method of claim 32, growing the oil-producing plant, harvesting the seed, and extracting the selenium-free oil from the seed.

35. A method of preparing selenium-free oil from selenium-enriched oil-producing plants grown in the presence of selenium comprising: coating seeds of an oil-producing plant using the method of claim 33, growing the oil-producing plant, harvesting the seed, and extracting the selenium-free oil from the seed.

* * * * *

UNITED STATES PATENT AND TRADEMARK OFFICE
CERTIFICATE OF CORRECTION

PATENT NO. : 6,058,649
DATED : May 9, 2000
INVENTOR(S) : Bittman et al.

It is certified that error appears in the above-identified patent and that said Letters Patent are hereby corrected as shown below:

ON THE TITLE PAGE:

ITEM [73] Assignees:

Delete "Her Majesty the Queen in right of Canada, as represented by the Minister of Agriculture; Agra-Food Canada, both of British Columbia, Canada" and replace with --HER MAJESTY IN RIGHT OF CANADA AS REPRESENTED BY AGRICULTURE AND AGRI-FOOD CANADA, of British Columbia, Canada--.

IN THE CLAIMS:

Claim 5, Col. 18, line 39, delete "like".

Claim 13, Col. 18, line 67, delete "calcium selenite, and the like" and replace with --and calcium selenite--.

Claim 27, Col. 20, line 5, delete "23" and replace with --25--.

Signed and Sealed this

First Day of May, 2001

Attest:

NICHOLAS P. GODICI

Attesting Officer

Acting Director of the United States Patent and Trademark Office